United States Patent [19]

Kelley

[11] Patent Number: 4,865,012
[45] Date of Patent: Sep. 12, 1989

[54] REUSABLE COLD PACK FOR MEDICAL USAGE

[76] Inventor: Jerry S. Kelley, 712 Locust St., Tallmadge, Ohio 44278

[21] Appl. No.: 646,816

[22] Filed: Sep. 4, 1984

[51] Int. Cl.⁴ .............................................. A61F 7/00
[52] U.S. Cl. .................................. 126/204; 126/263; 128/403; 604/291
[58] Field of Search ................ 220/3.1; 604/113, 291; 128/403, 402, 399; 126/263, 204; 206/484; 62/530, 457, 112

[56] References Cited

U.S. PATENT DOCUMENTS 1,716,551  6/1929  Hayes .................... 62/530
3,736,769  6/1973  Peterson ................. 62/530

Primary Examiner—Jerome L. Kruter
Attorney, Agent, or Firm—Oldham & Oldham Co.

[57] ABSTRACT

A thermo pack for heating or chilling body portions comprising a mixture of water, salt, cellulose and flour sealed in a pliable bag.

8 Claims, 1 Drawing Sheet

REUSABLE COLD PACK FOR MEDICAL USAGE

TECHNICAL FIELD

The present invention is in the field of thermo treatment of patients by application topically of transfer packs.

BACKGROUND ART

Ice packs and hot water bottles have been around for a long time. Their therapeutic usefulness for treatment of aches, pains, sprains, and the like, have taken on new significance in the field of medicine, particularly so-called sports medicine.

The healing process of torn muscle and connective tissue has been scrutinized by the practitioners of sports medicine to allow the recuperation of injured athletes as quickly as possible.

The severe stress imposed on particular body parts, especially joints, by modern sports, particularly professional and highly competitive sports, has subjected certain athletes to an almost constant recuperative regimen to restore vitality to the affected area.

It is unnatural for the body to be subjected to such strenuous repetitive action of a particular type. For example, pitching a baseball, or stroking a tennis ball employs a natural movement, but damage occurs when one does such activity in serious competition as a full time profession, or in the case of some joggers as an obsession.

Thermo packs from sub-freezing cold to almost scalding are used to speed and enhance the healing process. Some treatment regimens prescribe alternation of hot and cold to stimulate the restorative process.

The proliferation of clinics, wide spread participation by the public in serious competitive sports, and the like, have all created a need for thermo packs of the type of the present invention that are soft and pliable and safe to use at a wide variety of temperatures.

Natural and readily available materials are used in the thermo pack where possible and salt is used to possibly add a healing or restorative factor.

Some thermo packs heretofore designed to stay soft have used antifreeze liquids such as alcohol or ethylene glycol to keep the liquid of the pack soft even at sub-freezing temperatures.

Normally, the cold packs are stored in a freezer until used. Hot packs are heated normally on a stove in a container of water.

The problem with some of the additives mixed with water in the packs is that the alcohol, for example, may begin to boil prior to water and cause the pack to explode or leak by splitting a seam. Some packs change consistency across their usable temperature range.

The present pack employs salt at a saturated level to provide lowered freezing point.

The packs, of course, can be used for a variety of purposes by anyone, not just the serious athlete.

The saline of the present invention is mixed into a paste with cellulose and flour.

DISCLOSURE OF INVENTION

It is an object of the present invention to provide a thermo pack useful from about 0° F. to 160-180° F. for treatment of a variety of chronic ailments and injuries, chronic or traumatic.

It is an additional object of the present invention to incorporate materials safe to living tissue.

It is a further object of the present invention that the thermo pack be of low cost and long life upon repeated usage and temperature fluctuations.

It is yet another object of the present invention that the thermo pack be of materials and a consistency such that it is mush-like in texture to provide a soft, all covering contact with the affected area being treated.

It is another object of the invention that the pack be comfortable and pleasing to touch.

It is yet another object of the invention that the pack have a high coefficient of heat; that is, serve as a heat sink, i.e., that when it is cold, it tends to stay that way and likewise if hot, it holds a large quantity of heat energy. It is believed that the water-salt-cellulose-flour paste employed in the present invention meets that criteria better than other materials that could possibly be used.

In general, a thermo pack used for variant temperature treatment, comprises: a sealed bag of liquid paste wherein the paste comprises water saturated with common salt, shredded paper, and flour.

BEST MODE FOR CARRYING OUT THE INVENTION

Figure 1:
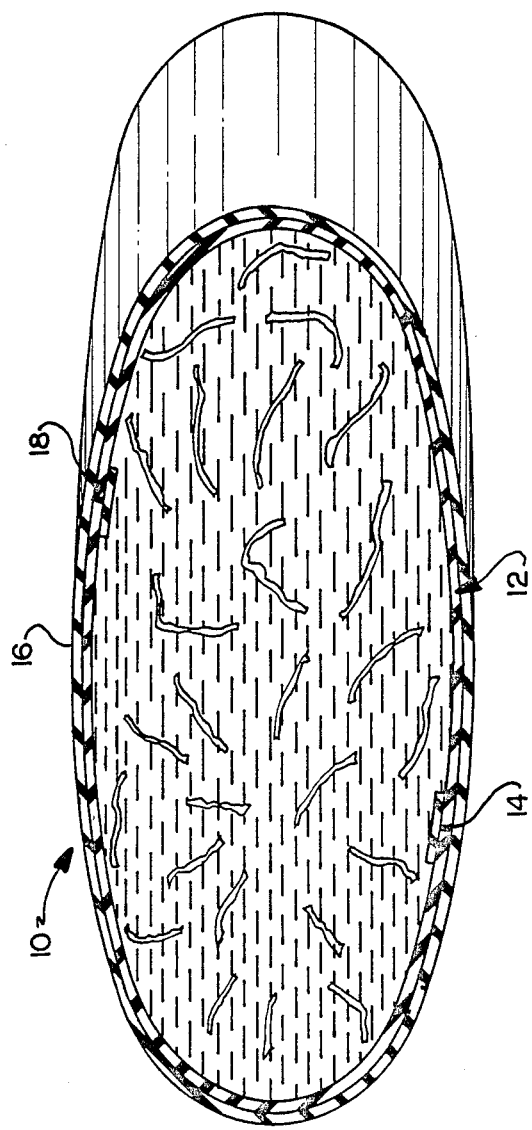
FIG. 1 is a cut-away perspective view of the thermo of the present invention.

The thermo pack 10 is comprised of a double bag surrounding a mushy paste. An inner bag 12 is heat sealed along an opening 14 after filling. An outer bag 16 is heat sealed along an opposite bag opening edge 18 after it is stretched over the inner bag.

The bags may be of any size and shape. Thermo pack could use a single layer bag of suitable film-like material that is capable of holding water without leakage and is able to withstand a temperature range of use of from around 0° F. to 160–180° F. and remain soft, pliable and strong.

The embodiment shown uses double bags of polyethylene film, FDA approved for safety to contact with skin. A low density polyethylene is used with 8 percent ethyl vinyl acetate added to improve strength and elasticity of the film.

In the preferred embodiment shown, the double bag consists of an inner bag, that is 6"×9.5" and the film thickness is 0.004 inch. The bag is open on one side for filling. Upon being filled, the open side is sealed closed by standard heat sealing methods.

The outer bag is of the same dimensions, but is of a 0.002 inch film thickness. It is stretched slightly to surround the inner bag and it also then is sealed along its open edge to complete sealing of the pack.

Both bags may be filled simultaneously and heat sealed along a common edge and still provide the benefits of double bagging.

The bag material could be of skin or animal membrane or of a natural material of some type to provide a product of all natural materials, particularly useful in some instances of prolonged exposure of the bag to sensitive skin areas of the patient, for example when rashes or bed sore type problems could occur.

A synthetic bag liner could be used to seal in the liquid with a natural exterior covering of cloth or suitable material to minimize aggravation to the patient's skin upon prolonged or frequent use in treatment of a serious chronic condition.

The contents of the thermo pack in the preferred embodiment are mixed by saturating a quantity of water with common salt, i.e., sodium chloride. The salt water solution is mixed to a specific gravity of about 1.125.

It should be pointed out that sea salt could be used just as easily or specialized salts such as copper salts or salts derived from so-called healing salt springs.

Commercial application dictates that specialized salts may be used simply because there are persons who strongly believe in the healing and/or curative powers of certain special salts or salt mineral combinations. There is, of course, some scientific indication of electron transfer and electrical properties associated with mineral salts that could plausibly occur through a water impermeable bag layer.

The consistency desired for the present invention is achieved in the preferred embodiment by addition of cellulose and flour to the saline solution. In the preferred embodiment, the mix is by weight as follows:

Saline 84.5 percent
Cellulose 8.3 percent
Flour 7.2 percent.

This mixture could be varied to some extent, but it has been found to provide a very satisfactory mushlike consistency that is unaffected by temperature. This same consistency across the full temperature range of use from around 0° F. to 160°-180° F. is very important in that it gives the thermo pack the desired comfortable feel and the optimum of physical surface contact against joint areas and contoured body portions to give maximum uniform heat (or cold) transfer into (or out of) the affected area.

The cellulose can consist of ground or shredded newsprint type paper or natural wood pulp. It could also be natural cellulose free of inks or fire retardants or chemicals harmful to the skin in the event of leakage.

The flour is added to give further body to the oatmeal consistency of the cellulose to give a final consistency somewhere between an oatmeal mush and a creamy paste.

This particular mixture exhibits extremely high heat or cold retention and the thermo packs of the present invention maintain effective, heat gradient between the affected body portion and the thermo pack for relatively very long periods of time.

The high cellulose-salt content of the mix compared to the flour provide a stable mixture wherein no spoilage or chemical transformation of the flour or other ingredients occurs.

While in accordance with the patent statutes, a preferred embodiment and best mode has been set forth in detail, the scope of the invention is limited solely by the scope of the appended claims.

What is claimed is:

1. A thermo pack used for variant temperature treatment, comprising:
   a sealed flexible bag containing a mixture having a mush-like to past consistency and comprising water, a salt dissolved therein, cellulose and flour, said cellulose and flour being present in amounts sufficient to impart the desired consistency.

2. A thermo pack as recited in claim 1, wherein the paste is made by the process of saturating the water with salt to an approximate specific gravity of 1.125, then mixing the resultant saline solution, paper and flour in the following proportions by weight: saline—84.5 percent, paper—8.3 percent, and flour—7.2 percent.

3. A thermo pack as recited in claim 1, wherein the paste is sealed in a first bag by heat sealing and said first bag is sealed into a second bag by heat sealing.

4. A thermo pack as recited in claim 3, wherein the bags are made of low density polyethylene film using vinyl acetate as a plasticizer.

5. A thermo pack as recited in claim 4, wherein the first bag has a greater film thickness than the second bag and the bag sizes are the same, the second bag stretching slightly to cover the first.

6. A thermo pack according to claim 1 in which said cellulose is shredded paper.

7. A thermo pack according to claim 1 in which said salt is common salt.

8. A thermo pack according to claim 7 in which said water and common salt form an essentially saturated solution.

* * * * *

UNITED STATES PATENT OFFICE
CERTIFICATE OF CORRECTION

Patent No. 4,865,012          Dated September 12, 1989

Inventor(s) Jerry S. Kelley

It is certified that error appears in the above-identified patent and that said Letters Patent is hereby corrected as shown below:

In column 4 line 16, delete the word "past" and insert therefore --paste--.

Signed and Sealed this

Twenty-eighth Day of August, 1990

Attest:

HARRY F. MANBECK, JR.

*Attesting Officer*          *Commissioner of Patents and Trademarks*